United States Patent
Wingate et al.

(10) Patent No.: US 10,547,953 B2
(45) Date of Patent: Jan. 28, 2020

(54) PORTLESS AND MEMBRANE-FREE MICROPHONE

(71) Applicant: Analog Devices, Inc., Norwood, MA (US)

(72) Inventors: David Wingate, Provo, UT (US); Isaac Chase Novet, Carlsbad, CA (US)

(73) Assignee: ANALOG DEVICES, INC., Norwood, MA (US)

(*) Notice: Subject to any disclaimer, the term of this patent is extended or adjusted under 35 U.S.C. 154(b) by 239 days.

(21) Appl. No.: 15/523,631

(22) PCT Filed: Nov. 9, 2015

(86) PCT No.: PCT/US2015/059666
§ 371 (c)(1),
(2) Date: May 1, 2017

(87) PCT Pub. No.: WO2016/077193
PCT Pub. Date: May 19, 2016

(65) Prior Publication Data
US 2017/0311090 A1    Oct. 26, 2017

Related U.S. Application Data

(60) Provisional application No. 62/077,448, filed on Nov. 10, 2014.

(51) Int. Cl.
*H04R 19/04* (2006.01)
*H04R 3/06* (2006.01)
(Continued)

(52) U.S. Cl.
CPC ............... *H04R 19/04* (2013.01); *G01L 9/12* (2013.01); *H04R 3/06* (2013.01); *H04R 19/005* (2013.01);
(Continued)

(58) Field of Classification Search
CPC .......... H04R 1/42; H04R 3/06; H04R 17/025; H04R 19/005; H04R 19/016; H04R 19/04;
(Continued)

(56) References Cited

U.S. PATENT DOCUMENTS 3,193,760 A * 7/1965 Smith, Jr. ................. G01L 9/12
                                                                73/304 R
4,312,024 A * 1/1982 Pest ....................... H01G 4/255
                                                                361/271
(Continued)

FOREIGN PATENT DOCUMENTS

| JP | 2013/251773 | 12/2013 |
|---|---|---|
| WO | 2016/077193 | 5/2016 |

OTHER PUBLICATIONS

International Search Report and Written Opinion issued in International Patent Application Serial No. PCT/US2015/059666 dated Feb. 19, 2016, 9 pages.
(Continued)

*Primary Examiner* — Davetta W Goins
*Assistant Examiner* — Daniel R Sellers
(74) *Attorney, Agent, or Firm* — Patent Capital Group

(57) ABSTRACT

Sound waves cause pressure changes in the air, and the pressure changes cause changes in the dielectric constant of air. Capacitive sensor measurements indicative of the changes in the dielectric constant of air can be processed to extract features associated with sound waves in the air. The features can include sound pressure levels represented and recordable as audio samples. Furthermore, the features can help identify types of sounds, determine direction of travel of the sound waves, and/or determine the source location of the audio. Instead of relying on movement of a mechanical member to transduce sound waves through a port into an electrical signal, an improved microphone uses capacitive
(Continued)

sensing to directly sample and sense static pressure as well as dynamic pressure or pressure changes in the air to derive audio samples. The resulting microphone avoids disadvantages of the conventional microphone having the moving mechanical member and port.

20 Claims, 14 Drawing Sheets

(51) Int. Cl.
  *G01L 9/12* (2006.01)
  *H04R 23/00* (2006.01)
  *H04R 19/00* (2006.01)

(52) U.S. Cl.
  CPC .... *H04R 23/006* (2013.01); *A61B 2562/0204* (2013.01)

(58) Field of Classification Search
  CPC ...... H04R 23/02; H04R 23/00; H04R 23/004; H04R 23/006; A61B 2562/0204; G01L 9/12
  USPC ................. 381/166–167, 173–175, 190–191
  See application file for complete search history.

(56) References Cited

U.S. PATENT DOCUMENTS

| | | | |
|---|---|---|---|
| 8,023,667 | B2 | 9/2011 | Lin |
| 2004/0228494 | A1* | 11/2004 | Smith ...................... A61B 7/04 381/67 |
| 2005/0151589 | A1* | 7/2005 | Fallesen ................... H03F 1/30 330/259 |
| 2006/0093161 | A1 | 5/2006 | Falcon |
| 2010/0254560 | A1* | 10/2010 | Mehregany .......... H04R 19/005 381/361 |
| 2010/0315272 | A1 | 12/2010 | Steele et al. |
| 2010/0329487 | A1* | 12/2010 | David .................... H03F 3/187 381/174 |
| 2011/0056302 | A1 | 3/2011 | Lutz |
| 2012/0057721 | A1* | 3/2012 | Arias-Drake ......... H04R 3/007 381/94.2 |
| 2015/0156576 | A1 | 6/2015 | Uchida et al. |

OTHER PUBLICATIONS

Ronald Miles et al., *A MEMS Low-Noise Sound Pressure Gradient Microphone with Capacitive Sensing*, Journal of Microelectromechanical Systems, Feb. 2015, 9 pages.

Michael B. Wakin et al., *An Architecture for Compressive Imaging*, Department of Electrical and Computer Engineering, Rice University, 1-4244-0481-9/06 © 2006 IEEE, ICIP 2016, 4 pages.

D. E. Aspnes, *Local-Field Effects and Effective-Medium Theory: A Microscopic Perspective*, Am. J. Phys, 50(8), Aug. 1982, © 1982 American Association of Physics Teachers, 6 pages.

M. J. Madsen et al., *Measuring the Molecular Polarizability of Air*, arXiv:0907.0782v1 [physics.optics] Jul. 6, 2009, 9 pages.

Eric W. Lemmon et al., *Thermodynamic Properties of Air and Mixtures of Nitrogen, Argon and Oxygen from 60 to 2000 K at Pressures to 2000 MPa*, 0047-2689/2000/29(3)/331/55, J. Phys, Chem. Ref. Data, vol. 29, No. 3, 2000, 55 pages.

S. Nir et al., *Polarizability Calculations on Water, Hydrogen, Oxygen, and Carbon Dioxide*, The Journal of Chemical Physics, vol. 59, No. 6, Sep. 15, 1973, 15 pages.

* cited by examiner

| SPL | Er | dEr/dSPL | log(dEr/dSPL) |
|---|---|---|---|
| 0 | 1.000051456378157000E+00 | | |
| 20 | 1.000051456378249000E+00 | 9.143796830812790000E-13 | -12.03887343 |
| 40 | 1.000051456379163000E+00 | 9.142464563183240000E-12 | -11.03893671 |
| 60 | 1.000051456388305000E+00 | 9.142597789946190000E-11 | -10.03893039 |
| 80 | 1.000051456479731000E+00 | 9.142597789946190000E-10 | -9.038930386 |
| 100 | 1.000051457393991000E+00 | 9.142597345856980000E-09 | -8.038930407 |
| 120 | 1.000051466536589000E+00 | 9.142597657194300000E-08 | -7.038930392 |
| 160 | 1.000052472225732000E+00 | 1.005689142674630000E-05 | -4.997536238 |
| 180 | 1.000061615163532000E+00 | 9.142937800676880000E-05 | -4.038914235 |
| 194.09373230 | 1.000102930411048000E+00 | 4.131524751569420000E-04 | -3.383889641 |

FIGURE 8

PORTLESS AND MEMBRANE-FREE MICROPHONE

CROSS-REFERENCE TO RELATED PATENT APPLICATIONS

This patent application claims priority to and/or receive benefit from U.S. Provisional Patent Application No. 62/077,448, titled "PORTLESS AND MEMBRANE-FREE MICROPHONE" and filed on Nov. 10, 2014. The Provisional Patent Application is hereby incorporated by reference in its entirety.

TECHNICAL FIELD OF THE DISCLOSURE

The present invention relates to the field of electronics, in particular to portless and membrane-free microphones based on capacitive sensing.

BACKGROUND

Microphones are ubiquitous and come in many forms. Conventional microphones are based on an acoustic-to-electric transducer which would include a mechanical member (e.g., a membrane or some other mechanical transducer) that would be displaced by pressure differences caused by sound waves. Besides the mechanical member, these microphones would usually include a port or porthole for allowing sound waves to reach the mechanical member in a controlled environment. The transducer would generate an electrical signal when the sound waves interact with the member. Effectively, the pressure differences caused by sound waves would move the member back and forth, and the movement of the member can modulate an electronic signal. For instance, the movement of the member can generate changes in electrical current, and that electrical current can be used as an electronic signal indicative of the sound waves in the air.

OVERVIEW

Sound waves cause pressure changes in the air, and the pressure changes cause changes in the dielectric constant of air. Capacitive sensor measurements indicative of the changes in the dielectric constant of air can be processed to extract features associated with sound waves in the air. The features can include sound pressure levels represented and recordable as audio samples. Furthermore, the features can help identify types of sounds, determine direction of travel of the sound waves, and/or determine the source location of the audio. Instead of relying on movement of a mechanical member to transduce sound waves through a port into an electrical signal, an improved microphone uses capacitive sensing to directly sample and sense static pressure as well as dynamic pressure or pressure changes in the air to derive audio samples. The resulting microphone avoids disadvantages of the conventional microphone having the moving mechanical member and port.

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which:

FIG. 8 shows a table relating sound pressure level to dielectric constants, according to some embodiments of the disclosure;

DESCRIPTION OF EXAMPLE EMBODIMENTS OF THE DISCLOSURE

Figure 1:
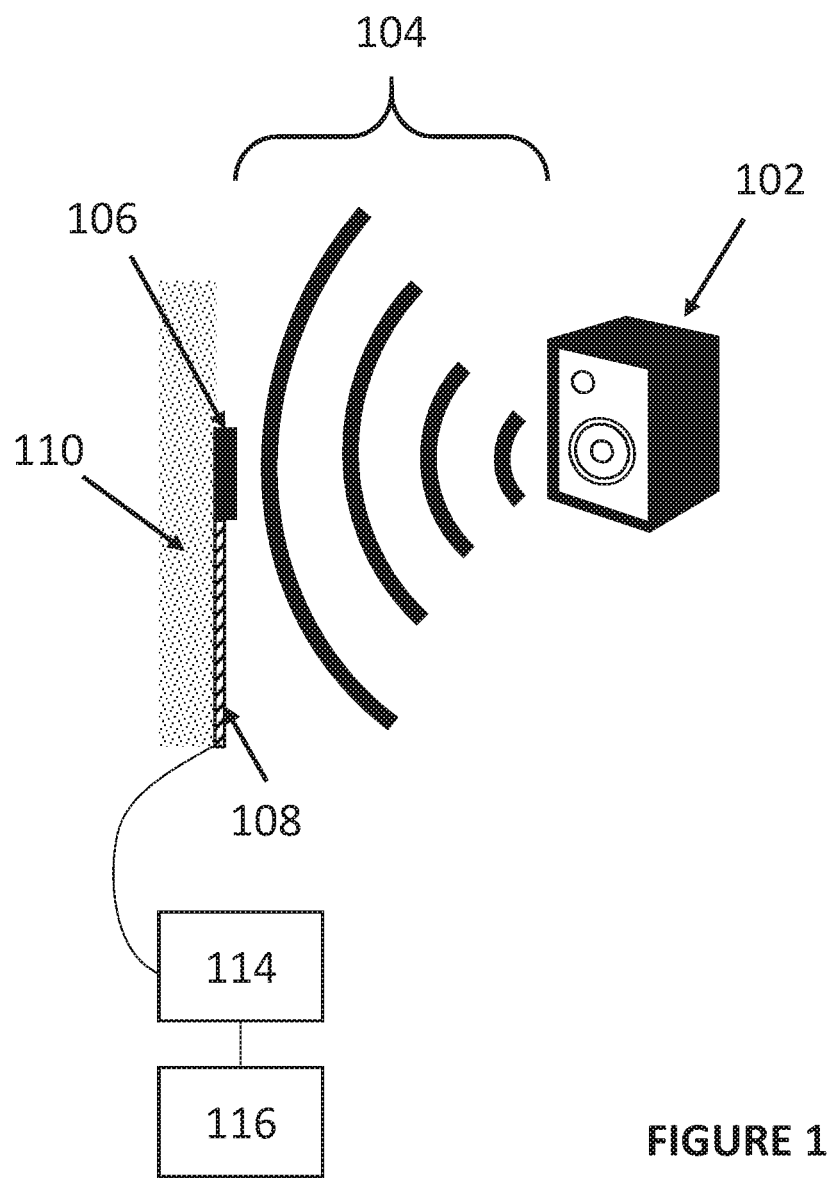
FIG. 1 shows an improved microphone having an exemplary capacitive sensor sensing of sound waves in the air, according to some embodiments of the disclosure.

Understanding Microphones that have a Movable Mechanical Transducer

Microphone technology has long relied upon a physical member—a mechanical transducer—for transducing energy of sound waves to an electrical signal. When sound waves travel in the air, the pressure changes can cause the physical member to move. A microphone can then translate that movement into an electrical signal that represents pressure change in the air, and thus enable the sound pressure at various instants to be recorded as audio samples. Varieties of microphones can differ depending on the mechanical transducer used. Examples include pressure-sensitive flexible/movable diaphragm forming one plate of a capacitor, pressure-sensitive flexible/movable diaphragm forming a part of an inductor, movable induction coil attached to a diaphragm, carbon granules pressed between two metal plates, piezoelectric materials responsive to pressure changes, reflective diaphragm, plane surfaces that vibrate due to sound, diaphragm holding liquid, etc. Many of these mechanical transducers are delicate devices prone to damage, and are typically not water-, or dirt-resistant (because such industrial designs can be difficult to achieve).

Unfortunately, relying on the mechanical transducer means these microphones have several inherent problems. More often than not, the microphones have to operate in a physically controlled environment, e.g., by providing a pathway, a port, or porthole, to ensure sound waves can properly arrive at the mechanical transducer. Moreover, users of these microphones and designers of these microphones would have to take measures to ensure the rather delicate mechanical transducer does not get damaged or dirty easily. Furthermore, these microphones have a limited range of operation, and typically would not work when the sound pressure level is too high (causing the movement of the mechanical transducer to stop, thereby leading to clipping or saturation of the audio signal). When the sound pressure is extremely high (e.g. explosions), the delicate mechanical transducer can break. For some microphones, aging of the mechanical transducer is also an issue, where, as the microphone becomes older, the mechanics may degrade, leading to a reduction in performance of the microphone.

The limitations of these microphones can be compared to limitations of a human ear with the ear drum being the mechanical transducer. The pathway to the ear drum, the ear canal, ensures the sound waves can arrive properly at the ear drum. When there is water, dirt, obstruction in the ear canal, hearing is impaired or affected. When the sound pressure level is too high, the ear's audio hearing system could "clip" or the ear drum can rupture or become damaged (e.g., temporary ringing, or permanent hearing damage). The human ear also suffers from aging of the human body, as evidenced by hearing loss in seniors. The human ear can also suffer from aging, or excessive use, e.g., with those exposed to loud sounds in the workplace.

Direct Sensing of Pressure Changes in the Air to Derive Sound Pressure Level

Instead of relying on a movable mechanical transducer to derive audio samples, an improved microphone can capacitively sense sound waves in the air directly. The capacitive sensor can sense static pressure and dynamic pressure changes in the air. FIG. 1 shows an improved microphone having an exemplary capacitive sensor sensing of sound waves in the air, according to some embodiments of the disclosure. The improved microphone can include a capacitive sensor directly exposed to pressure changes in the air near the capacitive sensor. This feature advantageously allows direct sampling of the sound pressure level in the air without the use of a mechanical transducer, thereby obviating at least some of the shortcomings described above. When sound waves creates different pressures in the air as the sound waves propagate, the capacitive sensor can sense the pressure changes and directly derive the sound pressure level.

To illustrate, FIG. 1 shows a source of sound 102 producing sound waves 104 in the air, and a capacitive sensor having a sensing portion 106 and one or more signal traces 108 for conducting an excitation signal to excite the capacitive sensor. The capacitive sensor is generally made of a conductive material. One or more signal traces 108 can be connected to first circuitry 114, which can be adapted for taking a capacitive measurement of the air near the sensing portion. The first circuitry 114 is connectable to second circuitry 116 for processing the capacitive sensor measurement as an audio sample.

At a given point in time, a sound wave varies the pressure in the air due to compression of the air at different points of a sound wave. Phrased differently, at a given point in time, pressure of the air in different points in space vary, and so do the dielectric constant. As the sound waves 104 moves through the air, the pressure of the air near the sensing portion 106 would change. When the pressure changes, the dielectric constant of the air near the sensing portion 106 would also change. The capacitive sensor, once excited, can build up an amount of charge on the surface of the sensing portion 106. Effectively, the capacitive sensor forms one of two plates of a virtual capacitor. A capacitor is characterized by its capacitance, which is related to the amount of electric charge on each plate divided by the voltage potential difference between the plates. Using the first circuitry 114, capacitive sensing can sense changes in the amount of charge on the surface of the sensing portion 106 in the form of current (or equivalently voltage), and derive the dielectric constant of the air as well as the pressure of the air near the sensing portion 106 (e.g., sound pressure level). Phrased differently, the technique of the improved microphone involves taking capacitive measurements and using the capacitive measurements to determine the sound pressure levels near the sensing portion 106 of the capacitive sensor. Using the second circuitry 116, the capacitive sensor measurements can be processed and stored as an audio sample. Besides deriving the dielectric constant and pressure of the air near the sensing portion, it is possible to derive dynamic changes in dielectric constant and dynamic pressure changes of the air near the sensing portion.

It can be demonstrated that the pressure changes and the dielectric constant of the air near the sensing portion 106 can be measured based on capacitance sensed by the capacitive sensor. The capacitive measurement is thus indicative of a dielectric constant of the air near the sensing portion 106, and the capacitive measurement is thus also indicative of a sound pressure level of the air near the sensing portion. These principles are described in further detail herein, by at least FIGS. 4-9 and the accompanying description.

The capacitive sensor can be any suitable self-capacitive element, where one side of the capacitive sensor structure will interface with some aspect of an electronic device (e.g., a mobile device, a television, etc.), and the opposite side of the sensor will interface with the surrounding air. Although not necessary, the sensing portion 106 and the one or more signal traces 108 can be mounted on non-conductive material 110 for stability or structure. The capacitive sensor does not have to be mounted on material 110, and can be alternatively exposed to the air on all sides, if desired (similar to an antenna).

The capacitive sensor can be exposed to the atmosphere in such a way that it is in close proximity to the atmosphere, but in some cases, can be shielded from direct contact with any humans or significant amounts of debris. The capacitive sensor does not include a moving member reactive to pressure changes in the air near the sensing portion to sense capacitance in the air near the sensing portion 106. Furthermore, it is possible to produce a microphone which does not include or is not placed next to a porthole (e.g., cavity, port, or pathway) for directing sound waves to the sensing portion 106.

The improved microphone can be made waterproof or even be used submerged in water or liquid, and would be less affected by the inherent shortcomings associated with a mechanical transducer. Without a port, the industrial/physical design of the microphone can be made simpler. The design of the microphone no longer has to consider the resonance of the pathway directing the sound waves. Also, there is no need to provide extra mechanisms to keep the microphone particle-free or dirt-free. It would be easy to integrate the capacitive sensor with other integrated circuits, and fabricate the capacitive-sensing based microphone (and associated circuitry) entirely on silicon substrate. The silicon substrate can easily accommodate multiple capacitive sensors, thus multiple microphones, all in a small package. Furthermore, the improved microphone directly sensing the sound pressure levels in the air can avoid the need to take into account a transfer function or a frequency response of the mechanical transducer (which generally requires filter(s) at the amplification stage in the sampling circuitry). Conventional microphones would normally have to consider or match how the mechanical transducer would behave at under different conditions, e.g., input frequency, etc. Without the physical limits of the mechanical transducer, the improved microphone would be less likely to clip or get damaged at extremely high sound pressure levels (e.g., above 140 sound pressure level (SPL)).

The improved audio sensing system can include one capacitive sensor or an array of capacitive sensors. For instance, the capacitive sensor(s) can be directly exposed to pressure changes in the air near the capacitive sensor. An exemplary capacitive sensor can include a sensing portion and a signal trace for conducting an excitation signal to excite the capacitive sensor. Further to the capacitive sensor(s), the audio sensing system can include a specialized analog to digital converter (ADC). The combination of the capacitive sensor(s) and the specialized ADC can serve to monitor fluctuations in the air density, and thus sound pressure levels. The operation of the combination can be aided by processing which can assist in creating sensor to converter transformations to acquire audio samples or an audio signal. In some embodiments, the audio sensing system can include first circuitry connectable to the capacitive sensor via the signal trace. The first circuitry can be adapted to take a capacitive measurement of the air near the sensing portion. The audio sensing system can further include second circuitry connectable to the first circuitry for processing the capacitive sensor measurement as an audio sample. Further details relating to the circuitries are explained in further detail in relation to FIG. 10.

Figure 2:
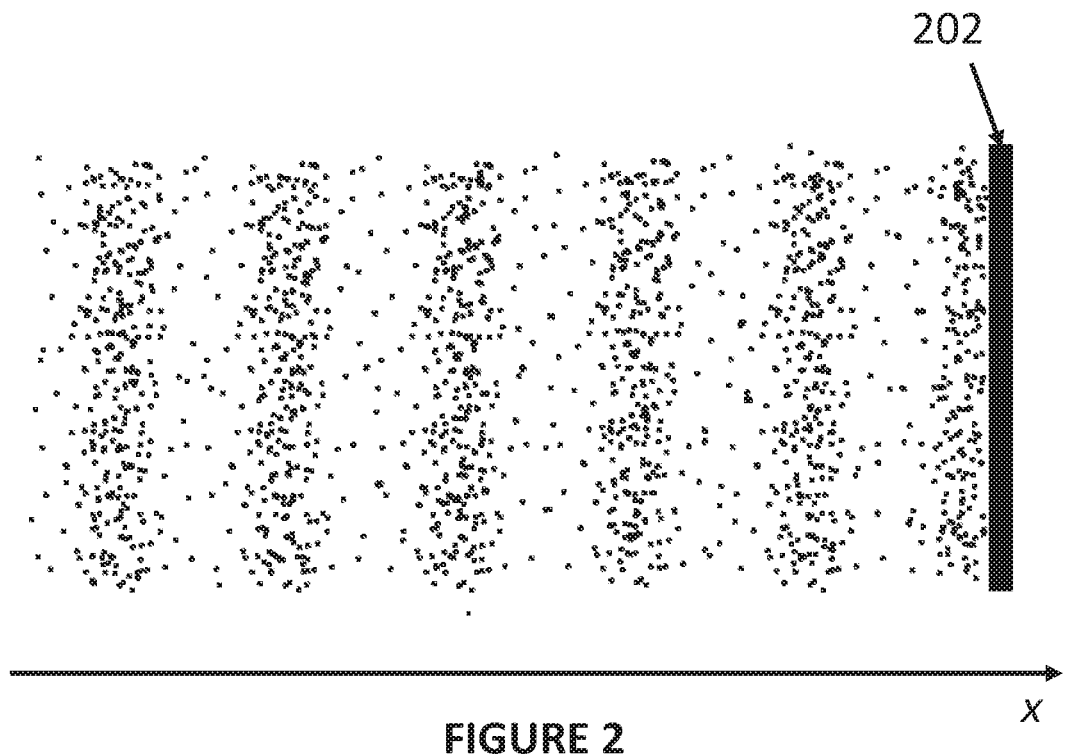
FIG. 2 shows an exemplary capacitive sensor and illustrative molecules in the air near the capacitive sensor, according to some embodiments of the disclosure.
Figure 3:
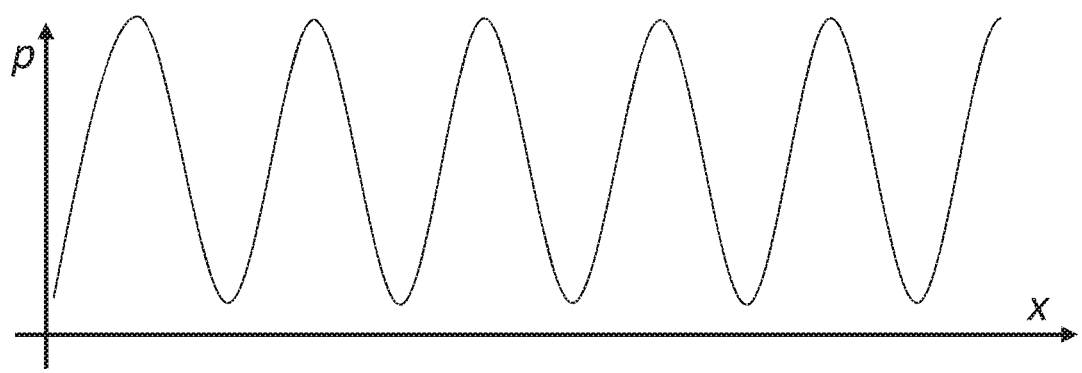
FIG. 3 shows an exemplary plot of pressure of the air near the capacitive sensor, according to some embodiments of the disclosure.

Physics of Sound Waves in the Air and their Relationship to Capacitive Measurements FIG. 2 shows an exemplary capacitive sensor and illustrative molecules in the air near the capacitive sensor 202, according to some embodiments of the disclosure. Corresponding to FIG. 2, FIG. 3 shows an exemplary plot of pressure of the air near the capacitive sensor 202, according to some embodiments of the disclosure. As the FIGURES show, as a sound wave generated by a source (originating from the left side of the FIGURE) moves through the air, the atmospheric pressure (having axis "p") surrounding the capacitive sensor 202 is modulated. Furthermore, as the sound wave travels towards the capacitive sensor 202, the pressure level near the capacitive sensor 202 would change over time (or over a plurality of capacitive measurements taken over time). The pressure variation from the resting level can generate some dielectric change in the air due to the fluctuation in density caused by the pressure change. The reasoning for the dielectric change with pressure is that the nitrogen and oxygen molecules (99% of air) increase or decrease their proximity to one another dependent on the local pressure. As proximity varies (having axis "x"), the electrostatic relationship of each molecule to the capacitive sensor varies. The net effect of having more or less molecules in a unit volume results in an increase or decrease, respectively, in the dielectric constant of the surrounding air.

In addition to the changing dielectric of the air, there can be some change in the mechanical structure of the sensor. For the present disclosure, the mechanical capacitive change is considered to be negligible. However, it is envisioned that some mechanical aspect of the sensor can be taken into account if desired, e.g., by providing a technique that can amplifying the pressure induced mechanical changes into an electrical signal.

The atmospheric condition being considered for the exemplary discussion includes dry, clean air at sea level. This condition serves as an exemplary condition (not a necessary condition), where a different atmospheric condition can be used in the following calculations. In any event, the atmospheric condition at sea level is explained herein due to its wide applicability because humans tend to live in lower elevation areas, with the world average being at 194 meters, which only creates a 1.8% reduction in atmospheric pressure. For this reason, the following calculations use standard pressure and room temperature. The water vapor content, although not considered in the following calculations, would only serve to scale the pressure varying values. For that reason, the following calculations can still provide a reasonable estimate of the dielectric change of the air without the addition of the vapor content.

Figure 4:
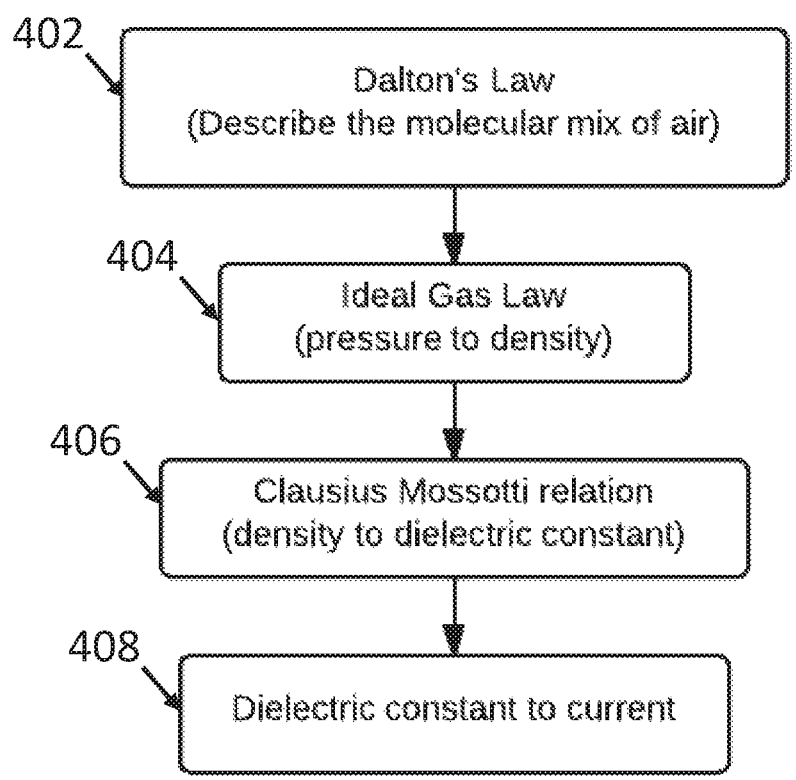
FIG. 4 illustrates the relationship of the molecular mix of particles to current sensed by a capacitive sensor, according to some embodiments the disclosure.

FIG. 4 illustrates the relationship of the molecular mix of particles to current sensed by a capacitive sensor, according to some embodiments the disclosure. The series of calculations based on the relationship can include four steps. In step 402, the air itself is be described as a mixture of two molecules, based on the constituent nitrogen and oxygen contributions to the fluid behavior using Dalton's law. In step 404, the change in air density versus air pressure is calculated using the Ideal Gas Law. In step 406, the air density information obtained from the Ideal Gas Law is used in the Clausius-Mossotti relation to determine the change in air's dielectric constant as air density changes. In step 408, the dielectric constant is related to a unit ampere change. After these four steps, it can be seen that static pressure and dynamic pressure changes, including the effect of sound induced air pressure changes, can be measured based on the current generated via capacitive sensing. Accordingly, an electrical signal generated by direct capacitive sensing of the air can be used as a basis for deriving an audio signal measuring the sound pressure levels.

For the calculations, several material constants are used (sourced from the National Institute of Standards and Technology):

air is approximately composed of:
78.12% nitrogen ($N_2$)
20.96% oxygen ($O_2$)
0.92% argon (Ar)
properties of air, oxygen, and nitrogen:
Air polarizability: $2.133*10^{-29}$ m3
Oxygen density: $1.33151*10^{-3}$ g/cm3
Molecular oxygen molar mass: 31.9988 g/mol
Molecular oxygen polarizability: $1.562*10^{-24}$
Nitrogen density: $1.16528*10^{-3}$ g/cm3
Molecular nitrogen molar mass: 28.0134 g/mol
Molecular nitrogen polarizability: $1.710*10^{-24}$ Referring back to step 402, Dalton's law can allow us to determine a single density for the $N_2+O_2$ composition that can be used as an approximation for clean, dry air. At standard temperature and pressure (STP), 1 mole of gas is equal to 22.4 liters:

Density of $O_2$=31.9988/22.4=1.429 g/L

Density of $N_2$=28.0134/22.4=1.251 g/L

Air density=[(0.7812*1.251)+(0.2096*31.9988)]/22.4=1.2767 g/L at STP

Air molar mass: 31.9988+28.0134=28.5824 g/mol

Convert the density to room temperature (25 C/298K) leads to the following:
Rearrange the ideal gas law to use density as a variable—
PV=nRT to P=$\rho R_{specific}$T
P is pressure of the gas;
V is volume of the gas;
n is the number of moles of gas;
R=ideal gas constant (product of the Boltzmann constant and the Avogadro constant $R$=8.314472(Pa*cm3)/(mol·K)

$\rho$ is density, to be determined
1 atm=101325 Pascal
$R_{specific}$ equals to R/M, where M is the molar mass of the gas
Find $R_{specific}$ of $N_2$ and $O_2$ $R_{specific}$ of $N_2$=(8.314472/0.0280134)=296.8034 (Pa*cm3)/(mol·K)

$R_{specific}$ of $O_2$=(8.314472/0.0319988)=259.8370 (Pa*cm3)/(mol·K)

Find the specific gas constant for the air approximation by multiplying the constituent gas constants by their unit volume:

$R_{specific}$=0.7812*$R_{specific}$ of $N_2$+0.2096*$R_{specific}$ of $O_2$=286.325(Pa*cm3)/(mol·K)

$\rho$=P/($R_{specific}$*T)=101325/(286.325*298.15)

Air density=1.1870 g/L@25 C sea level

Referring back to step 404, the ideal gas law is used to equate pressure to density. Density is a parameter in the calculation of the dielectric constant of the air approximation.

$P=\rho R_{specific} T \rightarrow P_{total} = \rho_{total} R_{specific} T$ $P_{total} = P_{ambient} + P_{sound}$ $P_{total} = R_{specific} T (\rho_{ambient} + \rho_{sound})$ $\rho_{total} = P_{total}/R_{specific} T$ Referring back to step 406, the Clausius-Mossotti relation creates a link between the densities constituent gasses in the air approximation mixture and the dielectric constant of the mixture:

$$\frac{\epsilon - 1}{\epsilon + 2} = \frac{4\pi}{3}(n_{O2}\alpha_{O2} + n_{N2}\alpha_{N2})$$

$n_{O2}$, $n_{N2}$ are the unit volume point densities of the oxygen and nitrogen molecules. The units of these values are molecules/volume, so density is restated in terms of molecular density (n/cm$^3$) rather than mass density (g/cm$^3$)
$\alpha_{O2}$, $\alpha_{N2}$ are material polarizability constants for the oxygen and nitrogen molecules.
$\epsilon$ is the dielectric constant of the oxygen and nitrogen mixture
Rearrange the relation to solve for $\epsilon$:

$$\epsilon = \frac{8\pi n_{O2}\alpha_{O2} + 8\pi n_{N2}\alpha_{N2} + 3}{-4\pi n_{O2}\alpha_{O2} - 4\pi n_{N2}\alpha_{N2} + 3}$$

Solve for $n_{O2}$ and $n_{N2}$.
State the calculation:
1 liter=1000 cm$^3$
density=g/L=g/1000 cm$^3$
molecular mass=g/mol $$N_a \frac{density}{molar\ mass} = mol^{-1} \frac{mol}{cm^3}$$

Nitrogen molecular density calculation:

$\rho$=1000*$P/RT$=101325/(296.8034*298.15)

$\rho$=1.1450/1000=0.00114502

($\rho$/mass)*(% composition)*$N_a$=(0.00114502/28.0134)* 0.7812*6.0221413*10$^{23}$= 1.9229159$E$+19 molecules/cm$^3$ Oxygen molecular density calculation $\rho$=1000*$P/RT$=1000*101325/(259.8370*298.15)

$\rho$=1.3079/1000=0.001307919

($\rho$/mass)*(% composition)*$N_a$=(0.001307919/31.9988)*0.2095*6.0221413*10$^{23}$=5.1592829$E$+ 18 molecules/cm$^3$ Air dielectric calculation $$\frac{\epsilon - 1}{\epsilon + 2} = \frac{4\pi}{3}(n_{O2}\alpha_{O2} + n_{N2}\alpha_{N2})$$

$n_{O2}$=5.1592829E+18
$\alpha_{O2}$=1.562E−24
$n_{N2}$=1.9229159E+19
$\alpha_{N2}$=1.71E−24
Air dielectric $\epsilon$=1.00051456378147E+00
In scientific notation herein, the letter E is used to mean "times 10 to the power of."
Referring back to step 408, it can be seen that the dielectric constant of air, which is measurable via capacitive sensing, is related to the sound pressure level (SPL) of the air. SPL or acoustic pressure (e.g., measured in pascals (Pa)) is the local pressure deviation from the ambient (average, or equilibrium) atmospheric pressure, caused by a sound wave. Generally, audio samples or components of an audio signal relate to the SPL at various instants in time. SPL is typically a logarithmic measure of the effective sound pressure of a sound relative to a reference value (e.g., 20 log of the ratio between the measured sound pressure level and reference value, sometimes referred as db SPL). It is measured in decibels (dB) above a standard reference level. In the following illustrative calculations, delta Er, the dielectric constant relative to the dielectric constant at 101325 Pa is defined as Er−Er(Ambient), or Er(101325+sound pressure in Pascal)−Er(101325).

Figure 5:
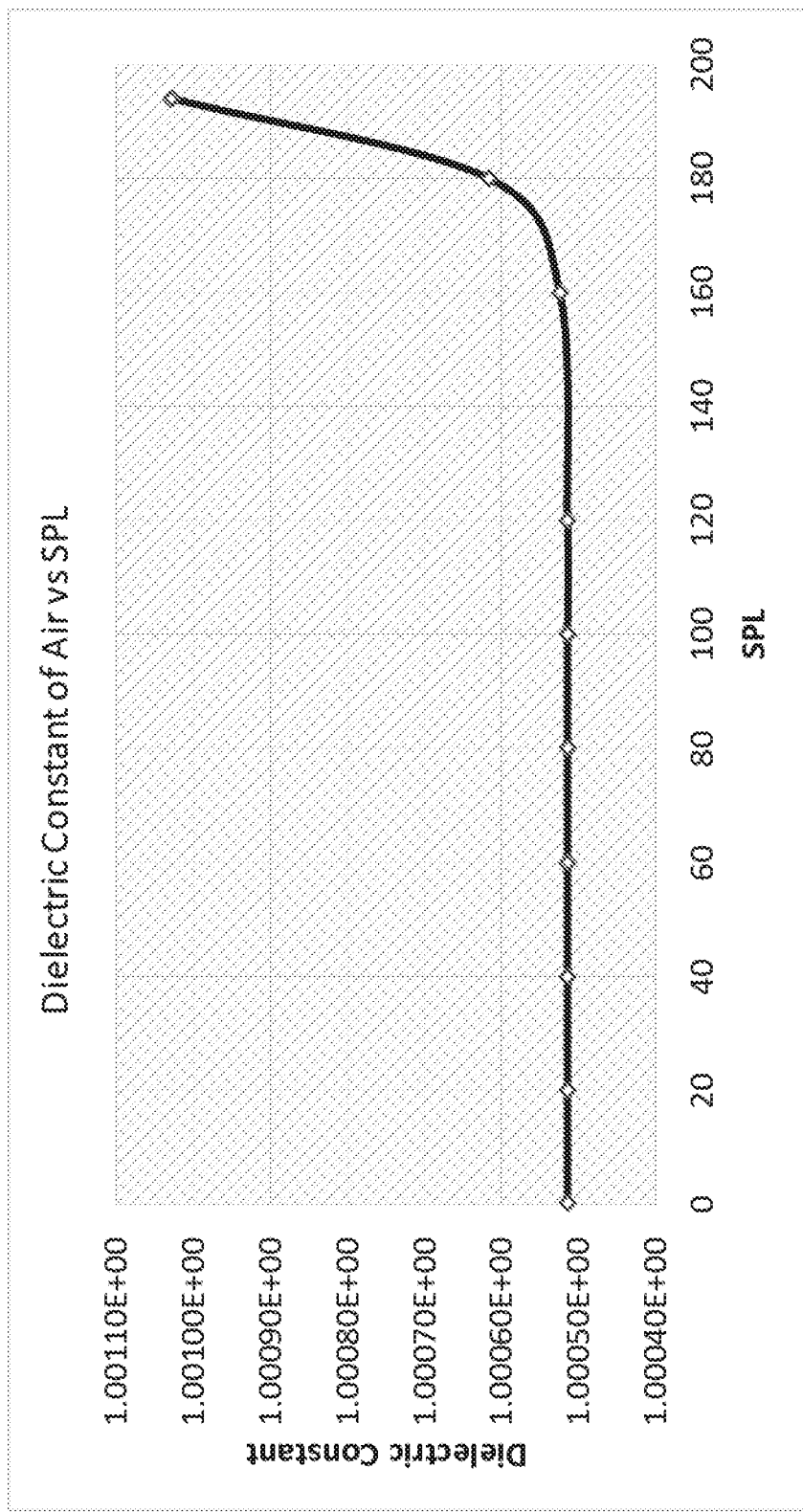
FIG. 5 shows a plot of dielectric constant per versus sound pressure level (SPL) decibel (dB), according to some embodiments the disclosure.
Figure 6:
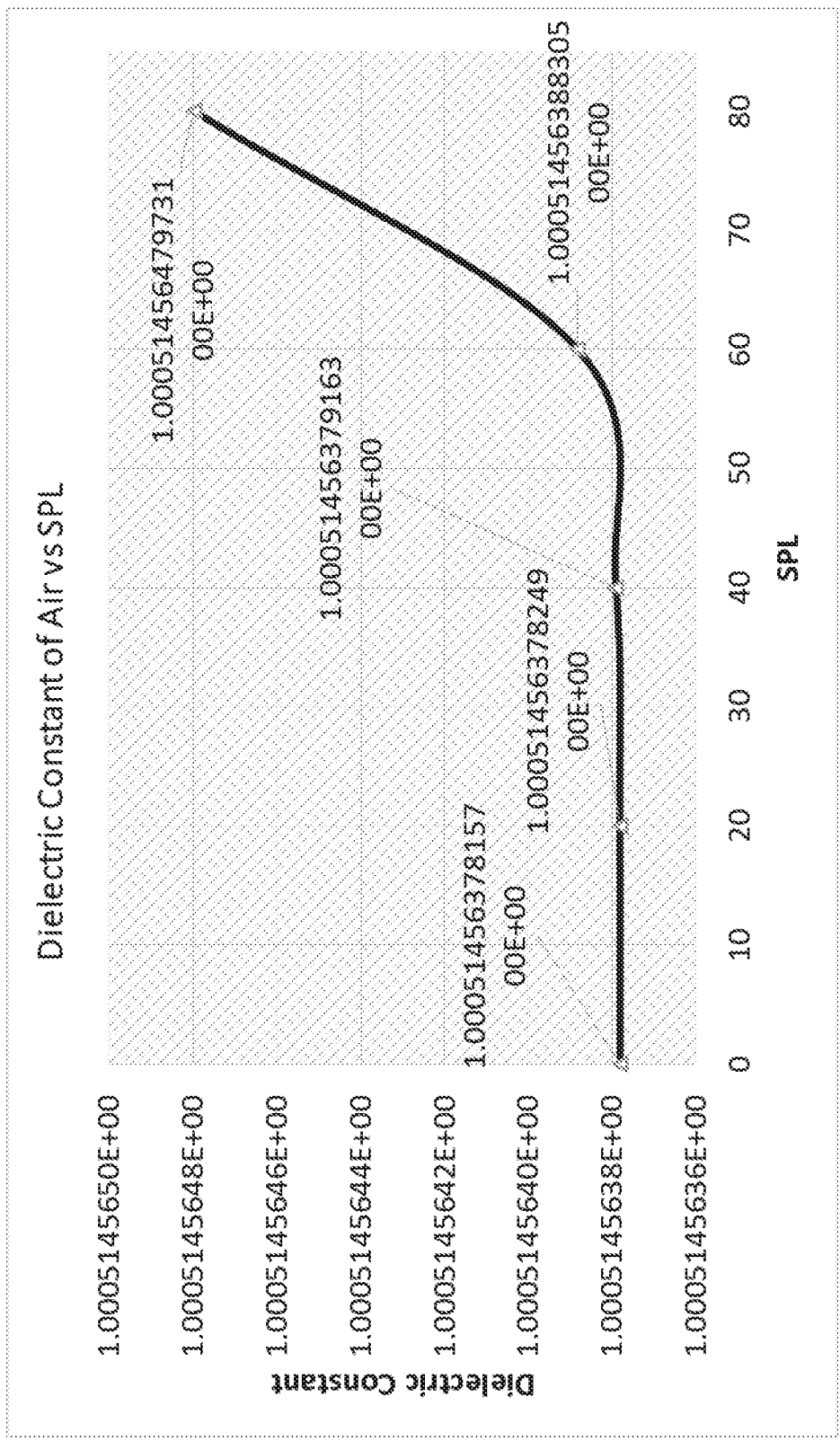
FIG. 6 shows another plot of dielectric constant per versus dB SPL, according to some embodiments the disclosure.
Figure 7:
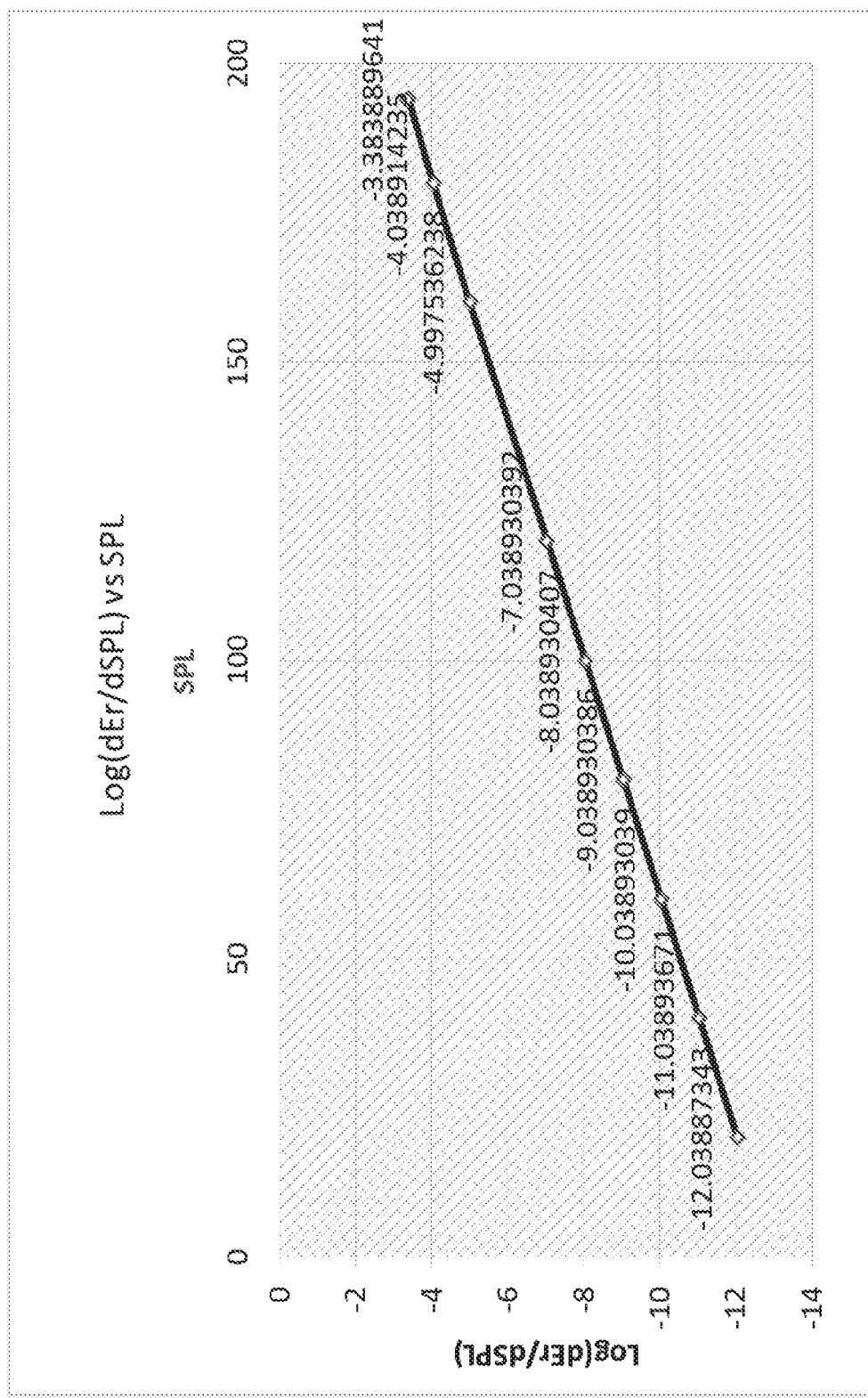
FIG. 7 shows a plot of dielectric constant in log scale versus dB SPL, according to some embodiments of the disclosure.

FIG. 5 shows a plot of dielectric constant Er per versus SPL decibel (dB), according to some embodiments the disclosure. FIG. 6 shows another plot of dielectric constant per versus dB SPL, according to some embodiments the disclosure (zoomed in to better show the change in dielectric constant in the lower dB SPL levels). FIG. 7 shows a plot of dielectric constant in log scale (log(dEr/dSPL)) versus dB SPL, according to some embodiments of the disclosure. FIG. 8 shows a table relating sound pressure level to dielectric constants, according to some embodiments of the disclosure (showing the data which generated the plots shown in FIGS. 5-7). It can be seen from the calculated numbers shown in FIGS. 5-8 that as the SPLs go up, it can be seen that dielectric constants also go up. The relationship can be used for the improved microphone to measure sound pressure level in the air for a given instant in time.

Figure 9:
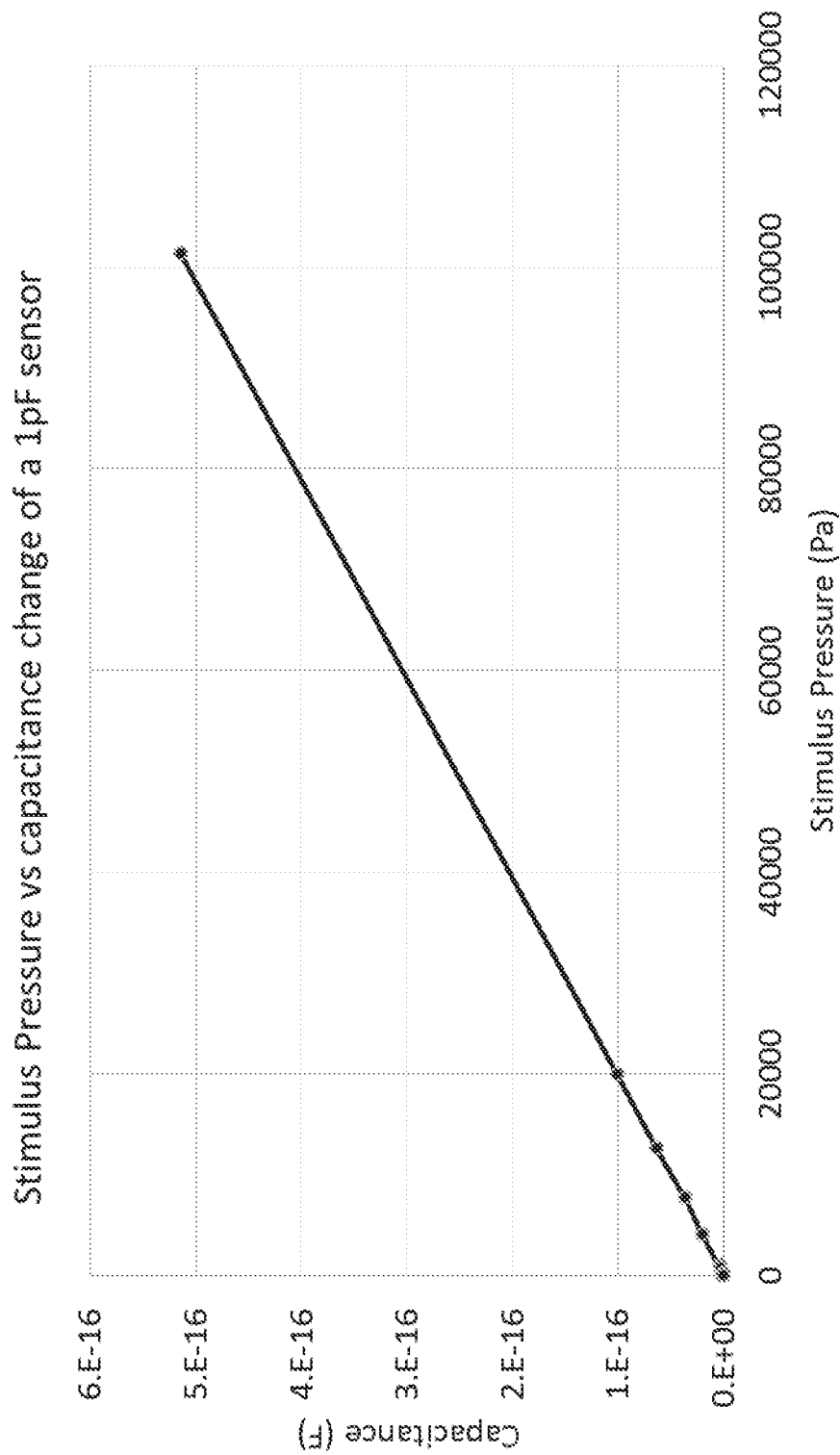
FIG. 9 shows a plot relating capacitance change versus sound pressure for a 1 picofarad air gap capacitor, according to some embodiments of the disclosure.

To further relate the dielectric constant of the air near a capacitive sensor to an actual capacitive measurement, the following calculations are performed based on an exemplary capacitive sensor having 1 picofarad (pF). FIG. 9 shows a plot relating capacitance (or capacitance change) versus sound pressure for a 1 picofarad air gap capacitor, according to some embodiments of the disclosure. Capacitance C can be computed based on the following exemplary relationship:

$$C = 8 * r * \epsilon_0 * \epsilon$$
$$= (8)(\text{radius of disk})(\text{relative permittivity of free space})$$
$$(\text{dielectric constant of air})$$

where dielectric constant of air is computed as described above as Er−Er(Ambient).

While the above relationship can be used for a disk sensor floating in air with nothing connected to it; the above relationship serves to illustrate changing dielectric values effecting the self-capacitance of an electrode (i.e., the sensing portion). It can be seen from the plot of FIG. 9 that the capacitance change can range from 10ths of yoctofarads to 100s of attofarads, for stimulus pressure that ranges from $2 \times 10^{-5}$ Pa (auditory threshold) to 101323 Pa (shockwave). Given the appropriate circuitry, the capacitive sensor can sense the change in dielectric constant and produce a current as the capacitive measurement in response to the stimulus pressure. Phrased differently, a capacitive sensor of the improved microphone can be sufficient to sense a range of dielectric fluctuations in the air caused by a variety of sounds. It is noted that the capacitive sensor can be used to sense, easily, maximum theoretical sound pressure levels without distortion (e.g., 194 dB SPL) since there is no mechanical component to limit capacitive transduction range, while many conventional microphones fail to sense sounds beyond 140 dB SPL. These sounds can include shockwaves, stun grenades, rifles, rocket launches, jet engines, etc. For that reason, the improved microphones can be particularly suitable for recording extremely loud sounds, e.g., for safety systems, aerospace systems, defense systems, etc.

Figure 10:
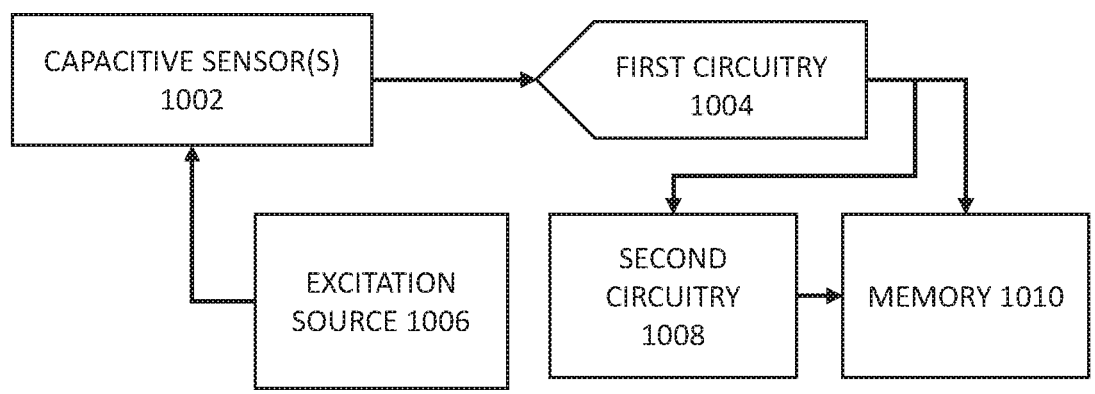
FIG. 10 shows an exemplary audio sensing system for producing audio samples via direct capacitive sensing of air, according to some embodiments of the disclosure.

Exemplary Circuitries and Methods for Taking Capacitive Measurements and Processing Thereof FIG. 10 shows an exemplary audio sensing system for producing audio samples via direct capacitive sensing of air, according to some embodiments of the disclosure. The audio sensing can produce audio samples or an audio signal via direct capacitive sensing of air. The audio sensing system can include one or more capacitive sensors 1002. An exemplary capacitive sensor is directly exposed to pressure changes in the air near the capacitive sensor, and can include a sensing portion and a signal trace for conducting an excitation signal from excitation source 1006 to excite the capacitive sensor. Further to the one or more capacitive sensor(s), the audio sensing system includes first circuitry 1004 connectable to the capacitive sensor via the signal trace. The first circuitry 1004 can be provided for taking a capacitive measurement of the air near the sensing portion. The audio sensing system further includes second circuitry 1008 connectable to the first circuitry 1004 for processing the capacitive sensor measurement as an audio sample (e.g., based on the relationship outlined in FIGS. 4-9). Both first circuitry 1004 and second circuitry 1008 can write to memory 1010 for storing capacitive measurements and/or derivations thereof.

Broadly speaking, the first circuitry 1004 provides a sampling mechanism that can suitably sample the capacitance or change in capacitance sensed by the capacitive sensor(s) 1002. The first circuitry 1004 can include a capacitance to digital converter, which can convert capacitance to a digital value. For instance, the first circuitry 1004 can include an integrating amplifier for integrating a signal on the signal trace, as generated by the capacitive sensor. Furthermore, the first circuitry 1004 can include an analog-to-digital converter for converting the output of the integrating amplifier into a digital sample representative of the capacitive sensor measurement.

In some embodiments, the first circuitry 1004 can include a charge integrating amplifier coupled with a specialized parallel filter to match the phase and frequency response of the charge integrating amplifier over a particular application's targeted bandwidth. The charge integrating amplifier and parallel filter can be simultaneously sampled by dual sample and hold circuits. The sample and hold circuits can then be digitized by a moderate resolution SAR ADC at a rate in excess of the application's signal bandwidth to facilitate oversampling.

The second circuitry can be provided to directly store the output of the first circuitry 1004 (e.g., capacitive measurements) as an audio sample in the memory 1010 (or some suitable memory element), or alternatively, provide one or more filters for process the output of the capacitive measurements to produce derivations of the capacitive measurements usable as audio samples. For instance, the capacitive measurements can be processed to produce sound pressure level measurements, based on the relationship outlined in FIGS. 4-9.

Note that, in some cases, the absence of a mechanical transducer in this improved audio sensing system makes the first and second circuitry simpler to design and implement than the circuitry used in conventional microphones.

Figure 11:
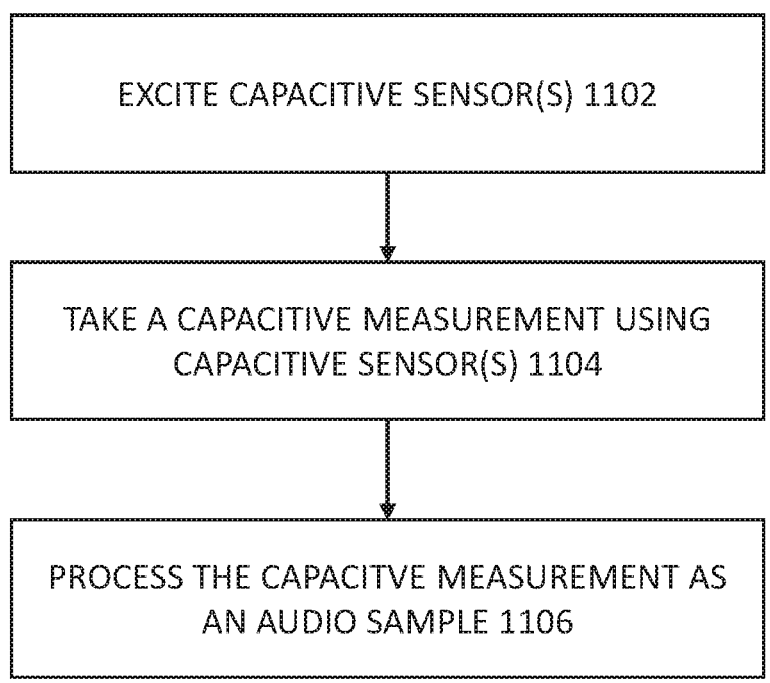
FIG. 11 shows a flow diagram illustrating a method for deriving audio samples via direct capacitive sensing of air, according to some embodiments of the disclosure.

FIG. 11 shows a flow diagram illustrating a method for deriving audio samples via direct capacitive sensing of air, according to some embodiments of the disclosure. The method includes exciting a capacitive sensor using an excitation signal (e.g., generated using excitation source 1106 of FIG. 10) (box 1102). As described herein, the capacitive sensor has a sensing portion and one or more signal traces for conducting the excitation signal to the sensing portion. More importantly, the capacitive sensor is directly exposed to pressure changes in the air near the sensing portion. The method further includes taking a capacitive measurement of the air near the sensing portion (box 1104). This part can be performed using first circuitry 1004 of FIG. 10, e.g., by integrating (using an integrating amplifier) a signal on the signal trace of the capacitive sensor and providing an output of the integrating amplifier to an analog-to-digital converter for converting the output of the integrating amplifier into a digital sample representative of the capacitive sensor measurement. The capacitive measurement can be indicative of a dielectric constant of the air near the sensing portion, and/or a sound pressure level of the air near the sensing portion. Furthermore, the method includes processing the capacitive sensor measurement as an audio sample (box 1106). This part can be performed using first circuitry 1008 of FIG. 10, e.g., by storing the capacitive sensor measurement and/or a derivation thereof as the audio sample in a memory element.

Array of Capacitive Sensors and Focused Capacitive Sensing

Figure 12:
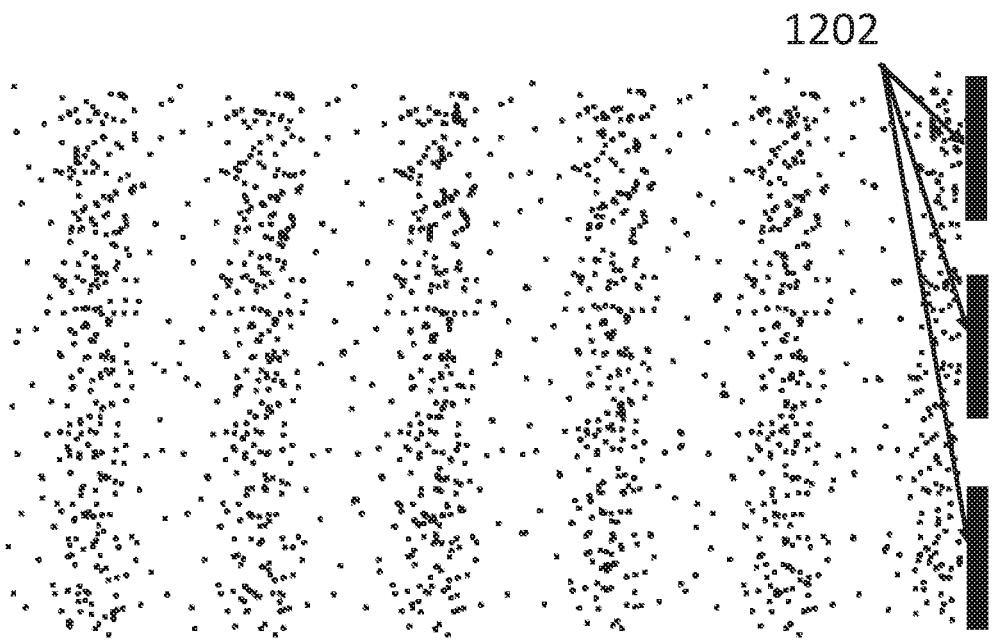
FIG. 12 shows multiple capacitive sensors sensing of sound waves in the air, according to some embodiments of the disclosure.

FIG. 12 shows multiple capacitive sensors sensing of sound waves in the air, according to some embodiments of the disclosure. In some embodiments, more than one capacitive sensors 1202 can be used (e.g., as an array of capacitive sensors) to sample the sound pressure level in the air near the capacitive sensors. The multiple measurements can be used to provide more sound pressure level information of the air near the capacitive sensors 1202. In some instances, the measurements can be used to decrease the level of noise by averaging capacitive measurements taken multiple sensors at the same time.

Figure 13:
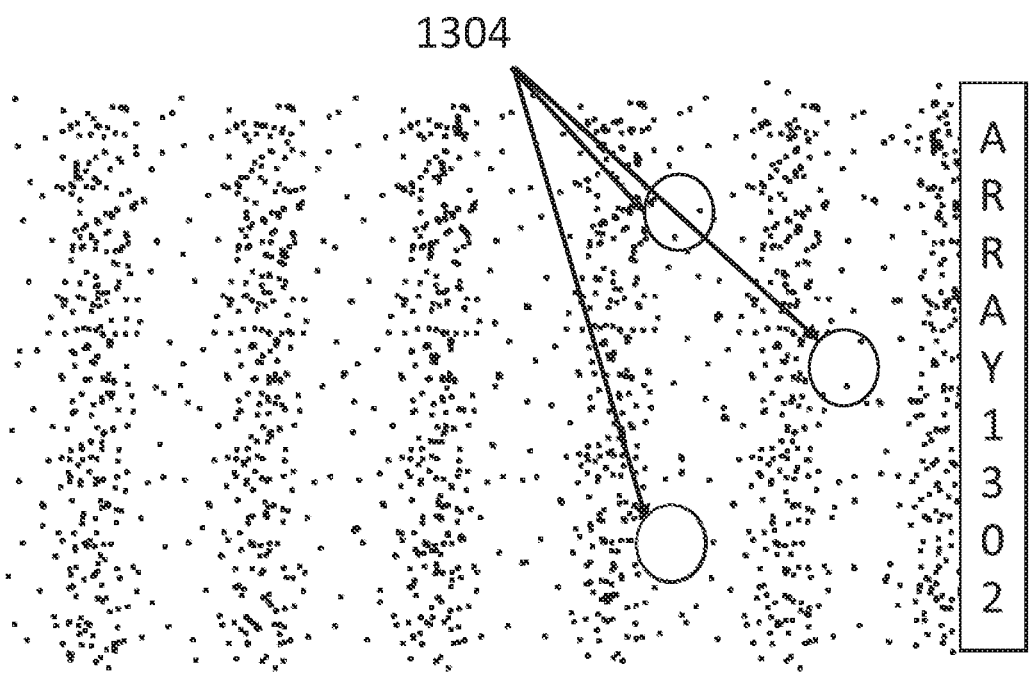
FIG. 13 shows an array of capacitive sensors providing focused capacitive sensing of sound waves in the air, according to some embodiments of the disclosure.

FIG. 13 shows an array of capacitive sensors providing focused capacitive sensing of sound waves in the air, according to some embodiments of the disclosure. Focused capacitive sensing is a technique which leverages an array of capacitive sensors 1302 to increase the response to the electric field generated by the array of capacitive sensors 1302, and in some cases, vary the electric field being generated systematically with codes or pseudo-randomized patterns. Using many capacitive sensors and special sets of excitation signals exciting the capacitive sensors, the capacitive sensors can generate specialized electrostatic fields, which can provide a focused measurement in regions such as exemplary regions 1304. Because the specialized electrostatic fields provide different views of the space, enhanced inferences about sound waves in the air can be made from measurements of responses to those specialized electrostatic fields. Selecting certain specialized electrostatic fields can allow the array of capacitive sensors to sense a focused region of the space for pressure changes in the air (providing a virtual microphone in the space). Repeating the steps with varied electrostatic fields can allow capacitive sensors to make enhanced inferences for many focused regions of the space, thereby increasing the resolution of capacitive sensing. Focused capacitive sensing is described in U.S. Provisional Application 62/060,884, which is hereby incorporated by reference in its entirety.

By generating special electric fields, a virtual microphone can be created on the fly. Such a technique can be particularly useful for beam forming or audio source separation and/or identification. Not only focused capacitive sensing can do audio sensing by focusing on one point, focused capacitive sensing allows the point to be programmatically set or determined. Effectively, the focused point can be moved to a suitable location on demand, or allow many focused points to exist at a given time. The microphone is effectively programmable to adjust to different scenarios, such as, when a person is nearby or not nearby, or when there are multiple speakers. Furthermore, the programmability of the microphone can allow the audio sensing system to learn and adjust the focused region to improve the quality of the audio samples. The same capacitive sensor(s), i.e., microphones, can be used for proximity sensing and/or human detection, in combination with audio sensing.

Exemplary Sensor Designs

It is important to note that the capacitive measurement depends on the design of the capacitive sensor (shape, form, design, size, material, etc.), which directly affects the capacitance of the capacitive sensor. Two exemplary variables can be used to increase the amount of charge developed on a sensor to increase the sensitivity of the capacitive sensor to sense capacitance changes in the air: voltage and sensor design/geometry. In some cases, the practical limit of sensor voltage is 45V, and is likely to be limited to 6V for some mobile devices. The sensor geometry is another variable, which may yield significant gains through various geometric arrangements.

The capacitive sensor or array of capacitive sensors can be designed like a patch antenna, but could take the shape of any structure which produces a large capacitive value in a small area or volume. If the sensor were two dimensional then it may be possible to apply the microphone in mechanically convenient places, like on screens or on the wall of an acoustic cavity.

For instance, some static planar shapes can achieve a self-capacitance value such that the extremely small changes in air pressure will influence the capacitive measurement. In some embodiments, the sensing portion comprises a two-dimensional planar structure attached to the signal trace. The two-dimensional planar structure can be adapted to generate an electric field in response to the excitation signal and sense a change in capacitance in response to pressure changes in the air near the sensing portion. In some cases, the sensing portion comprises a two-dimensional planar structure having one or more cut-outs. However, if a three dimensional mechanical structure were used, then the capacitance change per pressure could be greatly increased. For instance, the sensing portion can include a three-dimensional structure attached to the signal trace. The three-dimensional structure can be adapted to generate an electric field in response to the excitation signal and sense a change in capacitance in response to pressure changes in the air near the sensing portion. In some embodiments, the sensing portion comprises a three-dimensional structure having one or more cut-outs. A suitable three-dimensional sensing portion can maximize coplanar surface area, and also to maximize capture of fringe from the edge of a conductor onto the face of another.

Figure 14:
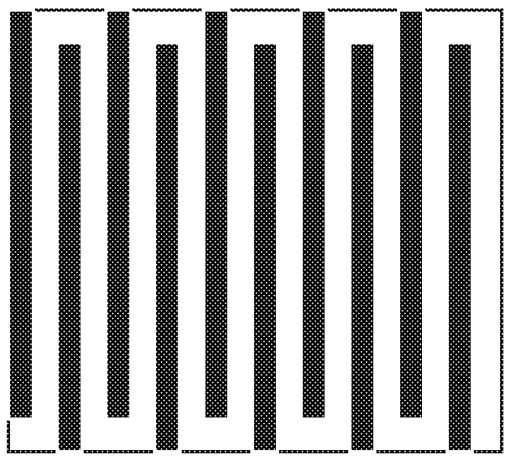
FIGS. 14-17 show exemplary designs of sensing portions of a capacitive sensor, according to some embodiments of the disclosure.
Figure 15:
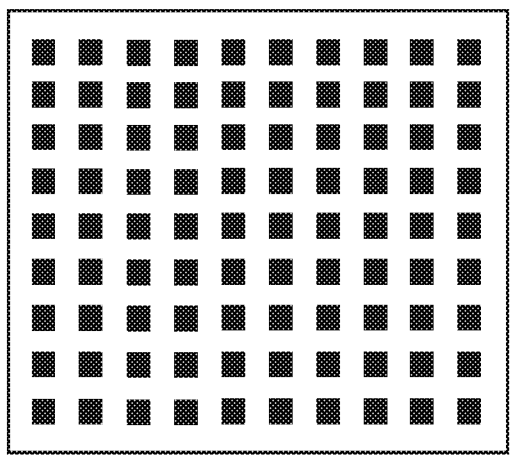
Figure 16:
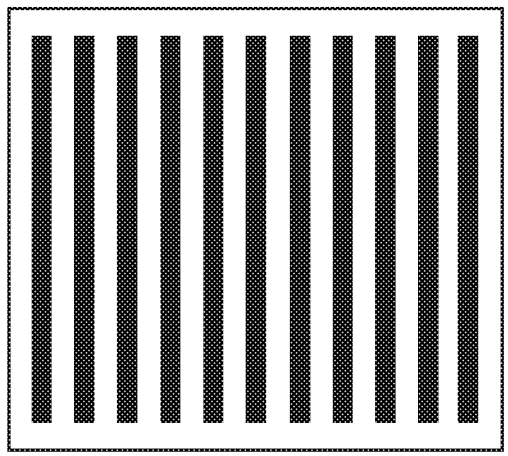
Figure 17:
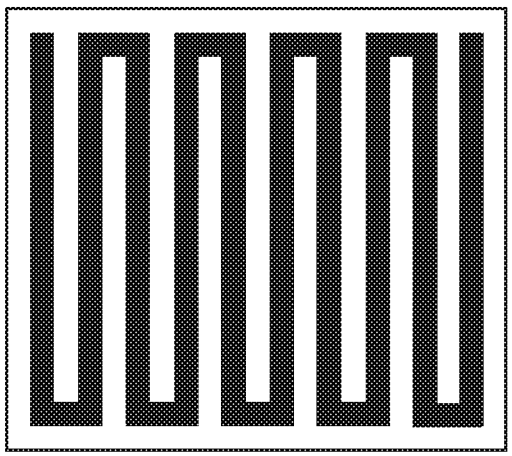

FIGS. 14-17 show exemplary designs of sensing portions of a capacitive sensor, according to some embodiments of the disclosure. FIG. 14 shows an exemplary square sensing portion having a serpentine shape (black portions illustrate cut outs). FIG. 15 shows an exemplary square sensing portion having cut outs in a grid pattern. FIG. 16 shows an exemplary square sensing portion having an array of lines as cutouts. FIG. 17 shows an exemplary square sensing portion having a cut out in a serpentine shape. Sensing portions shown in FIGS. 14-17 can span different shapes, such as circle, oval, ellipse, star, rectangle, pentagon, hexagon, heptagon, octagon, nonagon, decagon, irregular shape, etc. Depending on the application, the cut outs can differ.

Generally speaking, designs of the sensing portion can vary. In some designs, the sensing portion can include a single continuous conductor arranged in an advantageous manner to provide relatively high capacitance per area. In some designs, the sensing portion can include two or more continuous conductors (each having the same pattern, and in some cases, connected to each other) arranged in an advantageous manner to provide relatively high capacitance per area. In some designs, the sensing portion can include two or more continuous conductors having different patterns (in some cases, connected to each other) arranged in a mutually advantageous manner to provide relatively high capacitance per area.

Within the context of the disclosure, many embodiments of the improved microphone are described showing one sensing portion (e.g., one electrode) forming one plate of a virtual capacitor for directly sampling the dielectric change or pressure change in the air near the sensing portion. In some embodiments, the one or more sensing portions of the improved microphone can be connected to the same circuitry effectively forming one connected sensing portion for directly sampling the dielectric change or pressure change in the air near the sensing portions. In some further embodiments, the improved microphone may include two sensing portions (e.g., two electrodes) forming both plates of a capacitor for sensing the dielectric change or pressure change in the air between the two sensing portions. In such designs, the changes in dielectric constant in the air between the two sensing portions can lead to changes in capacitance of the two sensing portions. Changes in capacitance can be measured via capacitive sensing using the two sensing portions each connected to its own circuitry for taking a capacitive measurement. Accordingly, when the dielectric constant changes, two capacitive measurements can be taken by the two sensing portions. The two sensors can be used to directly sampling the dielectric change or pressure change in the air near the sensing portions, or can be used for purposes of calibrating the capacitive sensors, or to provide two internally consistent capacitive measurements.

Figure 18:
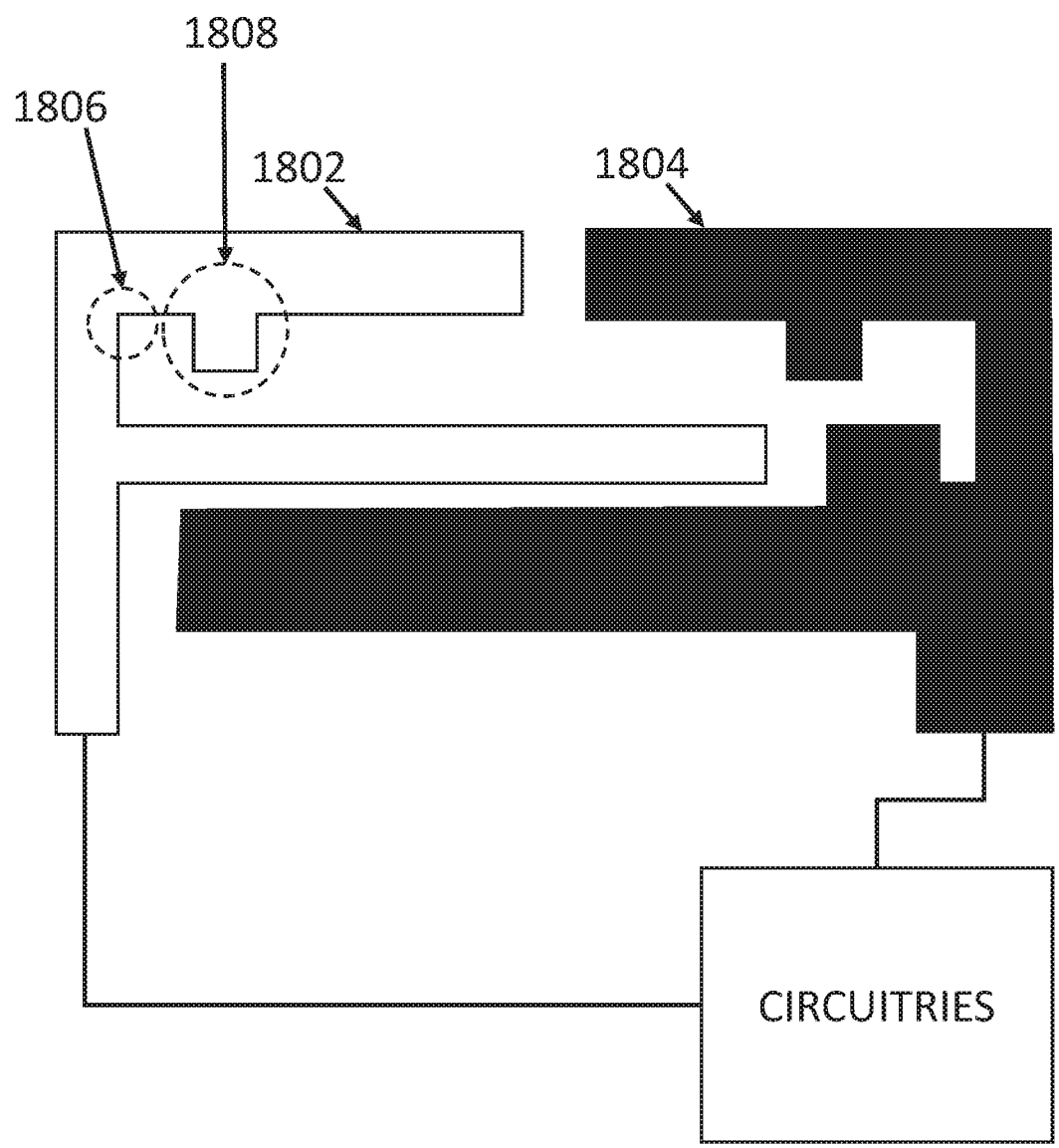
FIG. 18 shows another exemplary design of a capacitive sensor having at least one sensing portion, according to some embodiments of the disclosure.

FIG. 18 shows another exemplary design of a capacitive sensor having at least one sensing portion, according to some embodiments of the disclosure. The exemplary capacitive sensor has two (interdigitated) sensing portions 1802, 1804 forming two plates of a capacitive sensor, but in some embodiments, only one of the sensing portions can be used (forming one plate of a virtual capacitor can be used). It is noted that the sensing portions bend (e.g., forming corner 1806), and tab protrusion(s) (e.g., tab 1808) are placed near corners of the bends. Generally speaking, a field interruption caused by the change in direction of a conductive trace can be manipulated by selectively varying trace width near the bend, or by adding small tab(s) to the trace near the bend. As a result, the self-capacitance or the capacitance of the capacitive sensor can be increased (per area).

Many of the designs disclosed herein can be extended into a three-dimensional sensing portion. Three-dimensional capacitive sensors span different shapes, e.g., sphere, cube, arc, rectangular prism, cylinder, square pyramid, cone, etc. Cut outs can be provided in any suitable manner to increase the capacitance per volume. Some three-dimensional capacitive sensors may have a lattice structure, mesh structure, net structure, or irregular structure.

To reduce noise sources which can couple to the capacitive sensor, some capacitive sensor designs may include driven shields. In some other applications, the capacitive sensor can include a second signal trace alongside the first signal trace. The second signal trace is not connected the sensing portion, but it is connectable to the first circuitry. The first circuitry can be adapted to reject a common mode signal present on the first signal trace and the second signal trace via differential signaling. Effectively, noise sources coupled to the signal traces can be cancelled out.

Sensor Arrangement for Focused or Beamed Sensing

Figure 19:
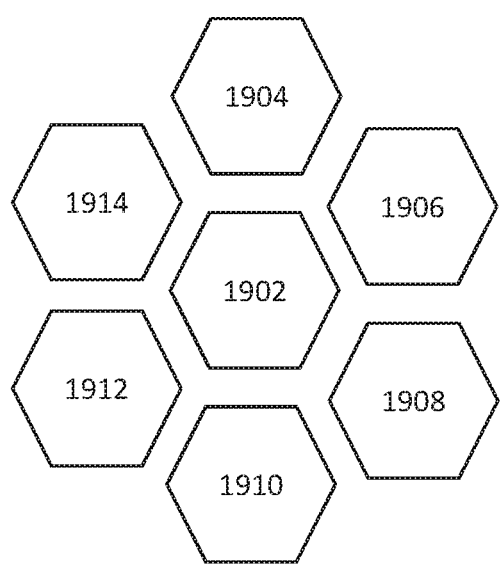
FIGS. 19-20 show illustrative sensor arrangements for generating a special electric field suitable for sensing sound waves in the air.
Figure 20:
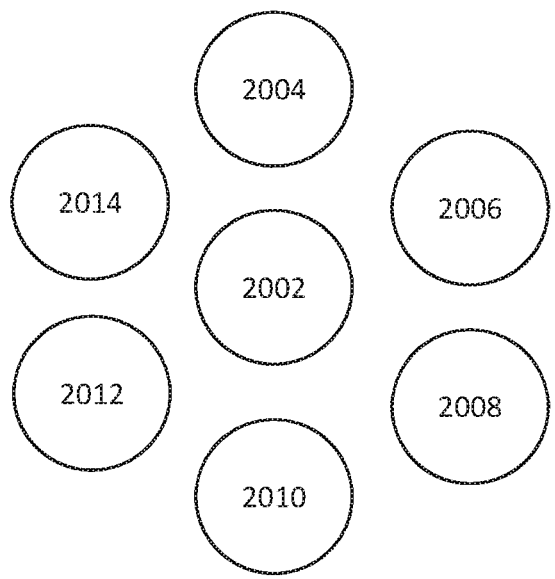

FIGS. 19-20 show illustrative sensor arrangements for generating a special electric field suitable for sensing sound waves in the air. In the example shown in FIG. 19, hexagon-shaped electrodes are used. Electrode 1902 serves as the main receiver electrode, and surrounding electrodes 1904, 1906, 1908, 1910, 1912, 1914 can be used to move the electric field surrounding the sensor arrangement. In the example shown in FIG. 20, circular-shaped electrodes are used. Electrode 2002 serves as the main receiver electrode, and surrounding electrodes 2004, 2006, 2008, 2010, 2012, 2014 can be used to move the electric field surrounding the sensor arrangement.

To change the electric field or a "beam" of the electric field, the surrounding electrodes can be excited to a different potential (e.g., a lower potential) from the potential of the main receiver electrode. The differences in potentials can grow or flatten portions of the electric field so that the electric field can become more sensitive to changes in dielectric constants in a particular area and/or particular direction (i.e., the changes in dielectric constants in the particular area and/or particular direction would elicit a bigger response/measurement). Since sound waves are directional, such a "beamformed" electric field can better sense sound waves from a particular direction (e.g., towards the source of the soundwaves) and become less sensitive to noise sources outside of the beam.

Figure 21:
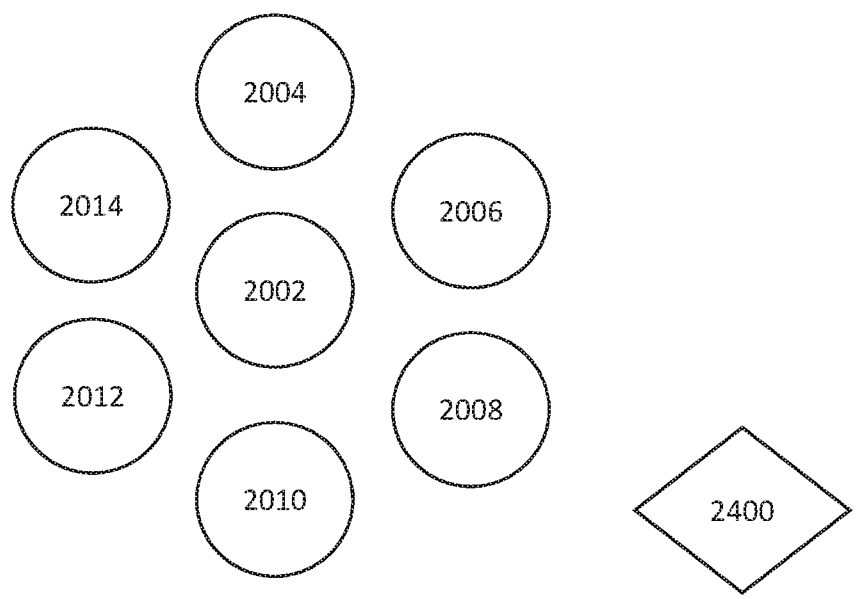
FIG. 21 shows an illustrative sensor arrangement for generating a special electric field that is less sensitive to interferers.

FIG. 21 shows an illustrative sensor arrangement for generating a special electric field that is less sensitive to interferers. Similar to example shown in FIG. 20, circular-shaped electrodes are used. Electrode 2002 serves as the main receiver electrode, and surrounding electrodes 2004, 2006, 2008, 2010, 2012, 2014 can be used to move the electric field surrounding the sensor arrangement. When a known interferer 2400 is near by the sensor arrangement, it is possible to excite certain ones of the surrounding electrodes to a different potential from the rest of the electrodes to move the "beam" of the electric field away from the interferer 2400. For instance, the electrodes 2008, 2006, and 2010 can be excited to a different potential (e.g., lower potential) to attenuate the electric field near the interferer.

When the electrodes are excited to different potentials, separate (and substantially simultaneous) capacitive sensing measurements can be made using the different electrodes, the capacitive sensing measurements can be provided as input to an electric field model to derive information of an object/stimulus disturbing the electric field. The electric field model can be defined based on the sensor arrangement and the potentials of the electrodes. In some cases, the relative position in N dimensions of a stimulus with respect to the sensor arrangement can be determined from the separate capacitive sensing measurements made by N+1 sensors.

Variations and Implementations

While capacitive sensors can be made of conductive materials such as copper or other metals, it is possible for capacitive sensors to be made of materials which are not as conductive as metals. In some cases, the capacitive sensors can be made of materials which can carry a lot of electrical charge and/or generate a strong electrostatic field. It is envisioned that advanced materials can be used for the capacitive sensors, e.g., such as materials which include carbon nanotubes or some other nanostructure to provide an extremely porous surface (e.g., a large surface area for storing or carrying charge). For instance, a "forest" of carbon nanotubes grown on an aluminum electrode can be used for the capacitive sensor to provide a relatively high capacitance per area. Broadly speaking, materials usable for the capacitive sensors can include any suitable metallic material, any suitable carbon-based material, indium tin oxide or other heavily doped semiconductor, any suitable conductive plastics, or any suitable conductive material usable as capacitive sensors.

Besides generating audio samples based on the capacitive measurements, it is possible for some embodiments to derive other features associated with sound waves in the air. For instance, the capacitive measurements can be provided to a thresholding circuit that can detect when the sound pressure level is too high. This can be used for hearing protection, or other safety applications. In some cases, the capacitive measurements can be used to identify or classify types of sounds. If multiple capacitive sensors are used (with or without focused capacitive sensing), the audio sensing system can infer direction of travel of the sound waves based on multiple capacitive measurements, and/or determine the source location of the audio.

Although not described above, it is envisioned by the disclosure that other sensors or data can be provided to the circuitries to improve audio sensing. For instance, humidity sensor can be used to adjust the dielectric, sound pressure level calculations based on the capacitive measurements. In some instances, calibration techniques can be implemented to reduce noise of the audio sensing system.

In certain contexts, the features discussed herein can be applicable to medical systems, scientific instrumentation, wireless and wired communications, radar, industrial process control, audio and video equipment, instrumentation, and other suitable systems using one or more microphones. Moreover, certain embodiments discussed above can be provisioned in technologies for medical imaging, patient monitoring, medical instrumentation, and home healthcare. This could include pulmonary monitors, heart rate monitors, pacemakers, etc. Other applications can involve automotive technologies for safety systems (e.g., driver assistance systems, infotainment and interior applications of any kind).

In yet other example scenarios, the teachings of the present disclosure can be applicable in the industrial markets that include process control systems that help drive productivity, energy efficiency, and reliability. Other consumer applications can include providing microphones in remote controllers, home theater systems, DVD recorders, high-definition televisions, digital displays, home appliances, etc. Yet other consumer applications can involve consumer electronics including portable electronics (handheld electronic devices, headsets, smartphones, tablets, watches, wearables), security systems, PCs, gaming technologies, virtual reality, simulation training, smart home systems, etc. The microphone(s) can be used for generating audio samples usable for voice command control systems. In some embodiments, supplemental circuitry can be provided to detect voice activity, classify voice commands, provide automatic speech recognition, etc. The microphone(s) can be provided on the same substrate as any associated circuitry to provide an audio module that can be easily fabricated and integrated into other systems.

In the discussions of the embodiments above, components can readily be replaced, substituted, or otherwise modified in order to accommodate particular circuitry needs. Moreover, it should be noted that the use of complementary electronic devices, hardware, software, etc. offer an equally viable option for implementing the teachings of the present disclosure.

Parts of various apparatuses for the audio sensing system can include electronic circuitry to perform the functions described herein. In some cases, one or more parts of the apparatus can be provided by a processor specially configured for carrying out some of the functions described herein, e.g., processing capacitive sensing measurements as audio samples. For instance, the processor may include one or more application specific components, or may include programmable logic gates which are configured to carry out the functions describe herein. The circuitry as described herein can operate in analog domain, digital domain, or in a mixed signal domain. In some instances, the processor may be configured to carrying out the functions described herein by executing one or more instructions stored on a non-transitory computer medium.

In one example embodiment, the circuitry of the FIGURES may be implemented as stand-alone modules (e.g., a device with associated components and circuitry configured to perform a specific application or function) or implemented as plug-in modules into application specific hardware of electronic devices. Note that particular embodiments of the present disclosure may be readily included in a system on chip (SOC) package, either in part, or in whole. An SOC represents an IC that integrates components of a computer or other electronic system into a single chip. It may contain digital, analog, mixed-signal, and often radio frequency functions: all of which may be provided on a single chip substrate. Other embodiments may include a multi-chip-module (MCM), with a plurality of separate ICs located within a single electronic package and configured to interact closely with each other through the electronic package. In various other embodiments, the audio sensing functionalities may be implemented in one or more silicon cores in Application Specific Integrated Circuits (ASICs), Field Programmable Gate Arrays (FPGAs), and other semiconductor chips.

In one example embodiment, any number of circuitry of the FIGURES may be implemented on a board of an associated electronic device. The board can be a general circuit board that can hold various components of the internal electronic system of the electronic device and, further, provide connectors for other peripherals. More specifically, the board can provide the electrical connections by which the other components of the system can communicate electrically. Any suitable processors (inclusive of digital signal processors, microprocessors, supporting chipsets, etc.), computer-readable non-transitory memory elements, etc. can be suitably coupled to the board based on particular configuration needs, processing demands, computer designs, etc. Other components such as external storage, additional sensors, controllers for audio/video display, and peripheral devices may be attached to the board as plug-in cards, via cables, or integrated into the board itself. In various embodiments, the functionalities described herein may be implemented in emulation form as software or firmware running within one or more configurable (e.g., programmable) elements arranged in a structure that supports these functions. The software or firmware providing the emulation may be provided on non-transitory computer-readable storage medium comprising instructions to allow a processor to carry out those functionalities.

It is also imperative to note that all of the specifications, dimensions, and spatial relationships outlined herein (e.g., the number of processors, logic operations, etc.) have only been offered for purposes of example and teaching only. Such information may be varied considerably without departing from the spirit of the present disclosure, or the scope of the appended claims (if any) and/or appended examples (if any). The specifications apply only to one non-limiting example and, accordingly, they should be construed as such. In the foregoing description, example embodiments have been described with reference to particular processor and/or component arrangements. Various modifications and changes may be made to such embodiments without departing from the scope of the appended claims (if any) and/or appended examples (if any). The description and drawings are, accordingly, to be regarded in an illustrative rather than in a restrictive sense.

Note that with the numerous examples provided herein, interaction may be described in terms of two, three, four, or more electrical components. However, this has been done for purposes of clarity and example only. It should be appreciated that the system can be consolidated in any suitable manner. Along similar design alternatives, any of the illustrated components, modules, and elements of the FIGURES may be combined in various possible configurations, all of which are clearly within the broad scope of this Specification. In certain cases, it may be easier to describe one or more of the functionalities of a given set of flows by only referencing a limited number of electrical elements. It should be appreciated that the electrical circuits of the FIGURES and its teachings are readily scalable and can accommodate a large number of components, as well as more complicated/sophisticated arrangements and configurations. Accordingly, the examples provided should not limit the scope or inhibit the broad teachings of the electrical circuits as potentially applied to a myriad of other architectures.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments.

It is also important to note that the functions related to audio sensing, illustrate only some of the possible functions that may be executed or performed by, or within, systems illustrated in the FIGURES. Some of these operations may be deleted or removed where appropriate, or these operations may be modified or changed considerably without departing from the scope of the present disclosure. In addition, the timing of these operations may be altered considerably. The preceding operational flows have been offered for purposes of example and discussion. Substantial flexibility is provided by embodiments described herein in that any suitable arrangements, chronologies, configurations, and timing mechanisms may be provided without departing from the teachings of the present disclosure. Numerous other changes, substitutions, variations, alterations, and modifications may be ascertained to one skilled in the art and it is intended that the present disclosure encompass all such changes, substitutions, variations, alterations, and modifications as falling within the scope of the appended claims (if any) and/or appended examples (if any). Note that all optional features of the apparatus described above may also be implemented with respect to the method or process described herein and specifics in the examples may be used anywhere in one or more embodiments.

Sample Embodiments

Example 1 is a microphone for direct capacitive sensing of sound waves in the air, the microphone comprising: a capacitive sensor directly exposed to pressure changes in the air near the capacitive sensor, said capacitive sensor having a sensing portion and a first signal trace for conducting an excitation signal to excite the capacitive sensor; and wherein: the first signal trace is connected to first circuitry for taking a capacitive measurement of the air near the sensing portion; and the first circuitry is connectable to second circuitry for processing the capacitive sensor measurement as an audio sample.

In Example 2, the microphone of Example 1 can include the capacitive measurement being indicative of a dielectric constant of the air near the sensing portion.

In Example 3, the microphone of Example 1 or 2, can include the capacitive measurement being indicative of a (static) sound pressure level of the air near the sensing portion.

In Example 4, the microphone of any one of the above Examples can include the capacitive sensor not including a moving member reactive to pressure changes in the air near the sensing portion to sense capacitance in the air near the sensing portion.

In Example 5, the microphone of any one of the above Examples can include the microphone not including or not being placed next to a porthole for directing sound waves to the sensing portion.

In Example 6, the microphone of any one of the above Examples can include the sensing portion comprising a two-dimensional planar structure attached to the signal trace, said two-dimensional planar structure adapted to generate an electric field in response to the excitation signal and sense a change in capacitance in response to pressure changes in the air near the sensing portion.

In Example 7, the microphone of any one of the above Examples can include the sensing portion comprising a two-dimensional planar structure having one or more cut-outs.

In Example 8, the microphone of any one of the above Examples can include the sensing portion comprising a three-dimensional structure attached to the signal trace, said three-dimensional structure adapted to generate an electric field in response to the excitation signal and sense a change in capacitance in response to pressure changes in the air near the sensing portion.

In Example 9, the microphone of any one of the above Examples can include the sensing portion comprising a three-dimensional structure having one or more cut-outs.

In Example 10, the microphone of any one of the above Examples can include the capacitive sensor further comprising a second signal trace alongside the first signal trace, the second signal trace not being connected the sensing portion, the second signal trace being connectable to the first circuitry; and the first circuitry rejecting a common mode signal present on the first signal trace and the second signal trace.

Example 11 is an audio sensing system for producing audio samples via direct capacitive sensing of air, the audio sensing system comprising: a capacitive sensor directly exposed to pressure changes in the air near the capacitive sensor, said capacitive sensor having a sensing portion and a signal trace for conducting an excitation signal to excite the capacitive sensor; first circuitry connectable to the capacitive sensor via the signal trace, said first circuitry for taking a capacitive measurement of the air near the sensing portion; and second circuitry connectable to the first circuitry for processing the capacitive sensor measurement as an audio sample.

In Example 12, the audio sensing system of Example 11 can further include the first circuitry comprising a capacitance to digital converter.

In Example 13, the audio sensing system of Example 11 or 12 can further include the first circuitry comprising an integrating amplifier for integrating a signal on the signal trace.

In Example 14, the audio sensing system of Example 13 can further include the first circuitry comprising an analog-to-digital converter for converting the output of the integrating amplifier into a digital sample representative of the capacitive sensor measurement.

In Example 15, the audio sensing system of any one of Examples 11-14 can further include the second circuitry storing the capacitive sensor measurement as an audio sample in a memory element.

Example 16 is a method for deriving audio samples via direct capacitive sensing of air, the method comprising: exciting a capacitive sensor using an excitation signal, wherein the capacitive sensor has sensing portion and a signal trace for conducting the excitation signal to the sensing portion, and the capacitive sensor is directly exposed to pressure changes in the air near the sensing portion; taking a capacitive measurement of the air near the sensing portion; and processing the capacitive sensor measurement as an audio sample.

In Example 17, the method of Example 16 can further include the capacitive measurement being indicative of a dielectric constant and/or the sound pressure level of the air near the sensing portion.

In Example 18, the method of Example 16 or 17 can further include taking the capacitive measurement of the air near the sensing portion comprising: integrating using an integrating amplifier a signal on the signal trace of the capacitive sensor.

In Example 19, the method of Example 18 can further include taking the capacitive measurement of the air near the sensing portion further comprising: providing an output of the integrating amplifier to an analog-to-digital converter for converting the output of the integrating amplifier into a digital sample representative of the capacitive sensor measurement.

In Example 20, the method of any one of Examples 16-19 can further include processing the capacitive sensor measurement as the audio sample comprising storing the capacitive sensor measurement as the audio sample in a memory element.

What is claimed is:

1. A microphone for direct capacitive sensing of sound waves in the air, the microphone comprising:
    a static capacitive sensor directly exposed to pressure changes in the air near the capacitive sensor, said static capacitive sensor having a sensing portion and a first signal trace for conducting an excitation signal to excite the static capacitive sensor; and
    wherein:
        the first signal trace is connected to first circuitry for taking a capacitive measurement of the air near the sensing portion; and
        the first circuitry is connectable to second circuitry for processing the capacitive sensor measurement as an audio sample.

2. The microphone of claim 1, wherein the capacitive measurement is indicative of a dielectric constant of the air near the sensing portion.

3. The microphone of claim 1, wherein the capacitive measurement is indicative of a sound pressure level of the air near the sensing portion.

4. The microphone of claim 1, wherein the static capacitive sensor does not include a moving member reactive to pressure changes in the air near the sensing portion to sense capacitance in the air near the sensing portion.

5. The microphone of claim 1, wherein the microphone does not include or is not placed next to a porthole for directing sound waves to the sensing portion.

6. The microphone of claim 1, wherein the sensing portion comprises a two-dimensional planar structure attached to the signal trace, said two-dimensional planar structure adapted to generate an electric field in response to the excitation signal and sense a change in capacitance in response to pressure changes in the air near the sensing portion.

7. The microphone of claim 1, wherein the sensing portion comprises a two-dimensional planar structure having one or more cut-outs.

8. The microphone of claim 1, wherein the sensing portion comprises a three-dimensional structure attached to the signal trace, said three-dimensional structure adapted to generate an electric field in response to the excitation signal and sense a change in capacitance in response to pressure changes in the air near the sensing portion.

9. The microphone of claim 1, wherein the sensing portion comprises a three-dimensional structure having one or more cut-outs.

10. The microphone of claim 1, wherein:
    the static capacitive sensor further comprises a second signal trace alongside the first signal trace;
    the second signal trace is not connected the sensing portion;
    the second signal trace is connectable to the first circuitry; and
    the first circuitry rejects a common mode signal present on the first signal trace and the second signal trace.

11. An audio sensing system for producing audio samples via direct capacitive sensing of air, the audio sensing system comprising:
    a static capacitive sensor directly exposed to pressure changes in the air near the static capacitive sensor, said static capacitive sensor having a sensing portion and a signal trace for conducting an excitation signal to excite the static capacitive sensor;
    first circuitry connectable to the capacitive sensor via the signal trace, said first circuitry for taking a capacitive sensor measurement of the air near the sensing portion; and
    second circuitry connectable to the first circuitry for processing the capacitive sensor measurement as an audio sample.

12. The audio sensing system of claim 11, wherein the first circuitry comprises a capacitance to digital converter.

13. The audio sensing system of claim 11, wherein the first circuitry comprises an integrating amplifier for integrating a signal on the signal trace.

14. The audio sensing system of claim 13, wherein the first circuitry comprises an analog-to-digital converter for converting the output of the integrating amplifier into a digital sample representative of the capacitive sensor measurement.

15. The audio sensing system of claim 11, wherein the second circuitry stores the capacitive sensor measurement as an audio sample in a memory element.

16. A method for deriving audio samples via direct capacitive sensing of air, the method comprising:

exciting a static capacitive sensor using an excitation signal, wherein the capacitive sensor has sensing portion and a signal trace for conducting the excitation signal to the sensing portion, and the static capacitive sensor is directly exposed to pressure changes in the air near the sensing portion;

taking a capacitive measurement of the air near the sensing portion; and processing the capacitive measurement as an audio sample.

17. The method of claim 16, wherein the capacitive measurement is indicative of at least one of a dielectric constant and sound pressure level of the air near the sensing portion.

18. The method of claim 16, wherein taking the capacitive measurement of the air near the sensing portion comprises:

integrating using an integrating amplifier a signal on the signal trace of the static capacitive sensor.

19. The method of claim 18, wherein taking the capacitive measurement of the air near the sensing portion further comprises:

providing an output of the integrating amplifier to an analog-to-digital converter for converting the output of the integrating amplifier into a digital sample representative of the capacitive measurement.

20. The method of claim 16, wherein processing the capacitive measurement as the audio sample comprises storing the capacitive measurement as the audio sample in a memory element.

* * * * *